United States Patent
Rajala et al.

[11] Patent Number: 6,074,333
[45] Date of Patent: Jun. 13, 2000

[54] MACHINE FOR CUTTING DISCRETE COMPONENTS OF A MULTI-COMPONENT WORKPIECE AND DEPOSITING THEM WITH REGISTRATION ON A MOVING WEB OF MATERIAL

[75] Inventors: Gregory John Rajala; Daniel James Oshefsky, both of Neenah; Thomas Raymond Holston, Appleton, all of Wis.

[73] Assignee: Kimberly-Clark Worldwide, Inc., Neenah, Wis.

[21] Appl. No.: 09/220,615

[22] Filed: Dec. 24, 1998

[51] Int. Cl.[7] .................................................. B31B 1/14
[52] U.S. Cl. .................. 493/346; 493/362; 493/365; 493/369; 493/370; 493/381; 493/938; 604/380
[58] Field of Search .................. 493/344–346, 493/362, 365, 379–381, 355, 937, 938, 464, 967; 604/358, 361, 365, 378, 380, 386, 387

[56] References Cited

U.S. PATENT DOCUMENTS

| | | | |
|---|---|---|---|
| Re. 29,365 | 8/1977 | Butler, Jr. | 242/58.3 |
| 2,254,217 | 9/1941 | Grupe | 493/333 |
| 2,958,365 | 11/1960 | Molins et al. | 154/36 |
| 3,139,243 | 6/1964 | Warwick et al. | 242/156.2 |
| 3,146,152 | 8/1964 | Seragnoli | 156/519 |
| 3,516,891 | 6/1970 | Hubin | 156/521 |
| 3,537,934 | 11/1970 | Munch | 156/364 |
| 3,582,437 | 6/1971 | Lenk | 156/521 |
| 3,645,463 | 2/1972 | Helm | 242/58.1 |
| 3,728,191 | 4/1973 | Wierzba et al. | 156/265 |
| 3,746,599 | 7/1973 | Peeters et al. | 156/505 |
| 3,758,367 | 9/1973 | Berg | 156/519 |
| 3,835,756 | 9/1974 | Bosse | 493/221 |
| 3,858,819 | 1/1975 | Bulter, Jr. | 242/58.3 |
| 3,879,246 | 4/1975 | Walker | 156/265 |
| 3,886,031 | 5/1975 | Taitel | 156/504 |
| 3,904,147 | 9/1975 | Taitel et al. | 242/156.2 |
| 3,918,655 | 11/1975 | Hillner et al. | 242/58.1 |
| 3,939,032 | 2/1976 | Taitel et al. | 156/505 |
| 3,957,570 | 5/1976 | Helm | 493/344 |
| 3,963,557 | 6/1976 | Patterson | 156/519 |
| 3,995,791 | 12/1976 | Schoppee | 242/58.1 |
| 4,010,911 | 3/1977 | Heitmann | 242/58.4 |

(List continued on next page.)

FOREIGN PATENT DOCUMENTS

| | | | |
|---|---|---|---|
| 0 677 378 A2 | 10/1995 | European Pat. Off. | B31B 1/90 |
| 0 692 375 A2 | 1/1996 | European Pat. Off. | B32B 31/00 |
| WO 94/02402 | 2/1994 | WIPO | B65H 39/14 |
| WO 95/19752 | 7/1995 | WIPO | B16F 13/15 |

*Primary Examiner*—Peter Vo
*Assistant Examiner*—Matthew Luby
*Attorney, Agent, or Firm*—Jerry F. Janssen

[57] ABSTRACT

The present invention provides a machine for cutting at least two components of a multi-component workpiece from webs of material which are moving at different speeds relative to one another, and depositing the two cut components on a third web of material moving at yet a different speed.

The machine cuts the first component from a moving first web, transfers the cut component to overlie a moving web of second material, and cuts the second component from the second web while the first component overlies and falls, either wholly or partially, within the cut boundaries of the second component. The mated first and second cut components are then transferred by the machine to a web of third material.

An optional embossing roller imparts a pattern to the stacked cut first and second components as they pass between the embossing and anvil rollers.

The machine is particularly adapted for the manufacture of articles of manufacture such as infant diapers, adult incontinence garments, and personal hygiene napkins in which elements of the napkin must be cut, registered with respect to one another, and affixed to other elements of the article during the manufacturing process.

22 Claims, 8 Drawing Sheets

U.S. PATENT DOCUMENTS

| | | | |
|---|---|---|---|
| 4,021,293 | 5/1977 | Total | 156/568 |
| 4,045,275 | 8/1977 | Stohlquist et al. | 493/333 |
| 4,061,527 | 12/1977 | Traise | 493/383 |
| 4,083,737 | 4/1978 | Foote, Jr. et al. | 156/73.1 |
| 4,120,739 | 10/1978 | Peeters et al. | 156/506 |
| 4,157,934 | 6/1979 | Ryan et al. | 156/504 |
| 4,190,475 | 2/1980 | Marschke | 156/157 |
| 4,190,483 | 2/1980 | Ryan et al. | 156/504 |
| 4,261,782 | 4/1981 | Teed | 156/361 |
| 4,262,855 | 4/1981 | Haag | 242/58.1 |
| 4,309,236 | 1/1982 | Teed | 156/164 |
| 4,364,787 | 12/1982 | Radzins | 156/164 |
| 4,371,417 | 2/1983 | Frick et al. | 156/495 |
| 4,374,576 | 2/1983 | Ryan | 242/58.4 |
| 4,404,058 | 9/1983 | Marchini | 156/571 |
| 4,443,291 | 4/1984 | Reed | 156/504 |
| 4,455,190 | 6/1984 | Bianchetto et al. | 156/504 |
| 4,481,053 | 11/1984 | Tokuno et al. | 156/157 |
| 4,525,229 | 6/1985 | Suzuki et al. | 156/161 |
| 4,572,043 | 2/1986 | Bianco | 83/18 |
| 4,578,133 | 3/1986 | Oshefsky et al. | 156/164 |
| 4,610,751 | 9/1986 | Eschler | 156/517 |
| 4,617,082 | 10/1986 | Oshefsky et al. | 156/447 |
| 4,645,554 | 2/1987 | Wyser | 156/159 |
| 4,719,855 | 1/1988 | Cannon et al. | 101/426 |
| 4,726,876 | 2/1988 | Tomsovic, Jr. | 156/552 |
| 4,762,582 | 8/1988 | de Jonckheere | 156/164 |
| 4,767,487 | 8/1988 | Tomsovic, Jr. | 156/256 |
| 4,769,098 | 9/1988 | Cederholm et al. | 156/159 |
| 4,776,911 | 10/1988 | Uda et al. | 156/161 |
| 4,776,920 | 10/1988 | Ryan | 156/504 |
| 4,795,510 | 1/1989 | Witrock et al. | 156/65 |
| 4,801,342 | 1/1989 | Wheeler et al. | 156/159 |
| 4,880,178 | 11/1989 | Goulette | 242/58.1 |
| 4,909,885 | 3/1990 | Swenson | 156/264 |
| 4,923,546 | 5/1990 | Wheeler et al. | 156/159 |
| 4,987,940 | 1/1991 | Straub et al. | 156/164 |
| 4,995,936 | 2/1991 | Cohn | 156/504 |
| 5,021,111 | 6/1991 | Swenson | 156/264 |
| 5,030,311 | 7/1991 | Michal et al. | 156/256 |
| 5,041,073 | 8/1991 | Eicker | 493/377 |
| 5,066,346 | 11/1991 | Long et al. | 156/157 |
| 5,091,039 | 2/1992 | Ujimoto et al. | 156/519 |
| 5,102,485 | 4/1992 | Keeler et al. | 156/256 |
| 5,102,486 | 4/1992 | Midgley et al. | 156/256 |
| 5,127,981 | 7/1992 | Straub et al. | 156/519 |
| 5,131,593 | 7/1992 | Siegfried et al. | 242/58.1 |
| 5,200,020 | 4/1993 | Collins et al. | 156/520 |
| 5,235,515 | 8/1993 | Ungpiyakul et al. | 364/469 |
| 5,244,530 | 9/1993 | Collins et al. | 156/519 |
| 5,261,996 | 11/1993 | Rossini | 156/521 |
| 5,286,543 | 2/1994 | Ungpiyakul et al. | 604/385.1 |
| 5,314,568 | 5/1994 | Ryan | 156/504 |
| 5,380,381 | 1/1995 | Otruba | 156/64 |
| 5,383,988 | 1/1995 | Hermann et al. | 156/64 |
| 5,407,507 | 4/1995 | Ball | 156/163 |
| 5,407,513 | 4/1995 | Hayden et al. | 156/265 |
| 5,413,651 | 5/1995 | Otruba | 156/64 |
| 5,415,716 | 5/1995 | Kendall | 156/256 |
| 5,492,591 | 2/1996 | Herrmann et al. | 156/538 |
| 5,549,783 | 8/1996 | Schroeder et al. | 156/542 |
| 5,552,007 | 9/1996 | Rajala et al. | 156/164 |
| 5,556,504 | 9/1996 | Rajala et al. | 156/519 |
| 5,562,793 | 10/1996 | Menard | 156/263 |
| 5,580,411 | 12/1996 | Nease et al. | 156/260 |
| 5,582,668 | 12/1996 | Kling | 156/161 |
| 5,591,297 | 1/1997 | Ahr | 156/521 |
| 5,595,335 | 1/1997 | Borel | 226/42 |
| 5,597,437 | 1/1997 | Lange et al. | 156/260 |
| 5,643,396 | 7/1997 | Rajala et al. | 156/361 |
| 5,659,538 | 8/1997 | Stuebe et al. | 364/469.02 |
| 5,660,657 | 8/1997 | Rajala et al. | 156/64 |
| 5,679,195 | 10/1997 | O'Dwyer et al. | 156/159 |
| 5,693,165 | 12/1997 | Schmitz | 156/164 |
| 5,695,846 | 12/1997 | Lange et al. | 428/98 |
| 5,702,551 | 12/1997 | Huber et al. | 156/73.1 |
| 5,705,013 | 1/1998 | Nease et al. | 156/260 |
| 5,716,478 | 2/1998 | Boothe et al. | 156/302 |

MACHINE FOR CUTTING DISCRETE COMPONENTS OF A MULTI-COMPONENT WORKPIECE AND DEPOSITING THEM WITH REGISTRATION ON A MOVING WEB OF MATERIAL

FIELD OF THE INVENTION

The present invention relates to a machine for cutting discrete parts of a workpiece traveling at different speeds relative to one another and applying the parts to a moving web of material. More particularly, the invention concerns a machine for cutting discrete parts from at least two webs of moving material moving at different speeds and depositing the discrete parts with controllable registration on a third continuously moving web of material.

BACKGROUND OF THE INVENTION

Articles such as infant diapers, adult incontinence garments, feminine napkins and the like have been manufactured generally by processes where discrete parts or components of the article are deposited on a continuously moving product web. Often, the speed with which the parts or components are produced and fed into the process is not the same as the speed of advance of the product web itself. In such cases, the speed of production and/or deposition of the component parts on the moving web must be varied to match the speed of the product web to properly match the parts to the moving web without adversely affecting the process or finished article.

Several methods for changing the speed of a part or component of material for deposition on a continuously moving web are known in the art. One method employs rollers segmented into sections which are inwardly and outwardly moveable in a direction radial to their direction of rotation. As the roller rotates, the segments are driven by cam actuating or gearing means to move inwardly and outwardly changing the linear surface speed of the roller segments as the roller rotates through each revolution.

Another method utilizes festoons to reduce the speed of the moving web to which the parts or components are to be applied. The continuously moving web is temporarily slowed to the speed of the component parts to be deposited, with the excess portion of the continuously moving web gathering in festoons. While the continuously moving web is slowed to match the speed of the component parts, the parts are transferred to the web and the speed of the web is then accelerated to un-gather the festoons prior to the next cycle.

Another method is the so-called "slip gap" method in which the parts or components are cut from a web of material moving at a slower speed than the product web. As the component parts are cut from the first web of material, they are held to the anvil roller by vacuum means. As the pieces pass tangentially to the continuously moving product web which is moving at a different speed, the parts or components slip temporarily until they are vacuum transferred from the anvil roller to the continuously moving product web.

These known methods of transferring component parts, moving at one speed, to a continuously moving web moving at a different speed, do not address the problem of insuring careful registration of the deposited component parts on the continuously moving web. The problem is exacerbated when the need exists for depositing two or more components, one on top of the other on the continuously moving web while insuring careful registration of one component to the other, or to the moving web.

There remains a need for an efficient machine for cutting and depositing workpiece components moving at different web speeds on a substrate web which machine insures accurate registration of the parts with respect to one another.

SUMMARY OF THE INVENTION

The present invention provides a machine for manufacturing a multi-component product comprising at least two components cut from moving webs of material. The individual components each have a shape and associated dimensions, a leading and a trailing edge, a longitudinal center line, and a longitudinal center defined by a point midway on said longitudinal center line between the leading and trailing edges. The machine cuts a first component from a first web of material, and then transfers the cut component to overly a second web of material. The machine next cuts a component from the second web of material while the first component overlies the second component during the cutting operation. The machine permits independent registration of the two components with respect to one another and, following their being cut, deposits the registered components on a web of moving material.

The machine comprises a) a first apparatus for cutting first component from a first web of material moving at a first speed and transferring the first component to overly a second web of material moving at a second speed; b) a second apparatus for receiving the cut component from the first apparatus on the second web of material and for cutting a second component from the second web while the first cut component overlies the second component, and for transferring the first and second cut components to a web of material moving at a third speed.

The machine provides drive means for independently driving the first and second cutting apparatuses, and means for adjusting the longitudinal center points of the first and second cut components with respect to one another. In a preferred embodiment, the means for adjusting the longitudinal center points of the two cut components comprises a phase shift differential apparatus. The phase shift differential apparatus permits the relative positioning of the cut first and second components so that the first component may lie wholly or partially within the cut boundaries of the second component.

The cutting blades on the two cutting apparatuses have predetermined shapes, with associated dimensions. In a preferred embodiment, the cutting blades on the first and second cutting apparatuses are of similar shapes, with the dimensions of the first component cutting blade being less than the corresponding dimensions of the second component cutting blade. In a particularly preferred embodiment, the two components are of the same shape, with the dimensions of the first cut component being less than those of the second cut component, with the first cut component being positionally centered on the cut second component.

BRIEF DESCRIPTION OF THE DRAWING FIGURES

Figure 1:
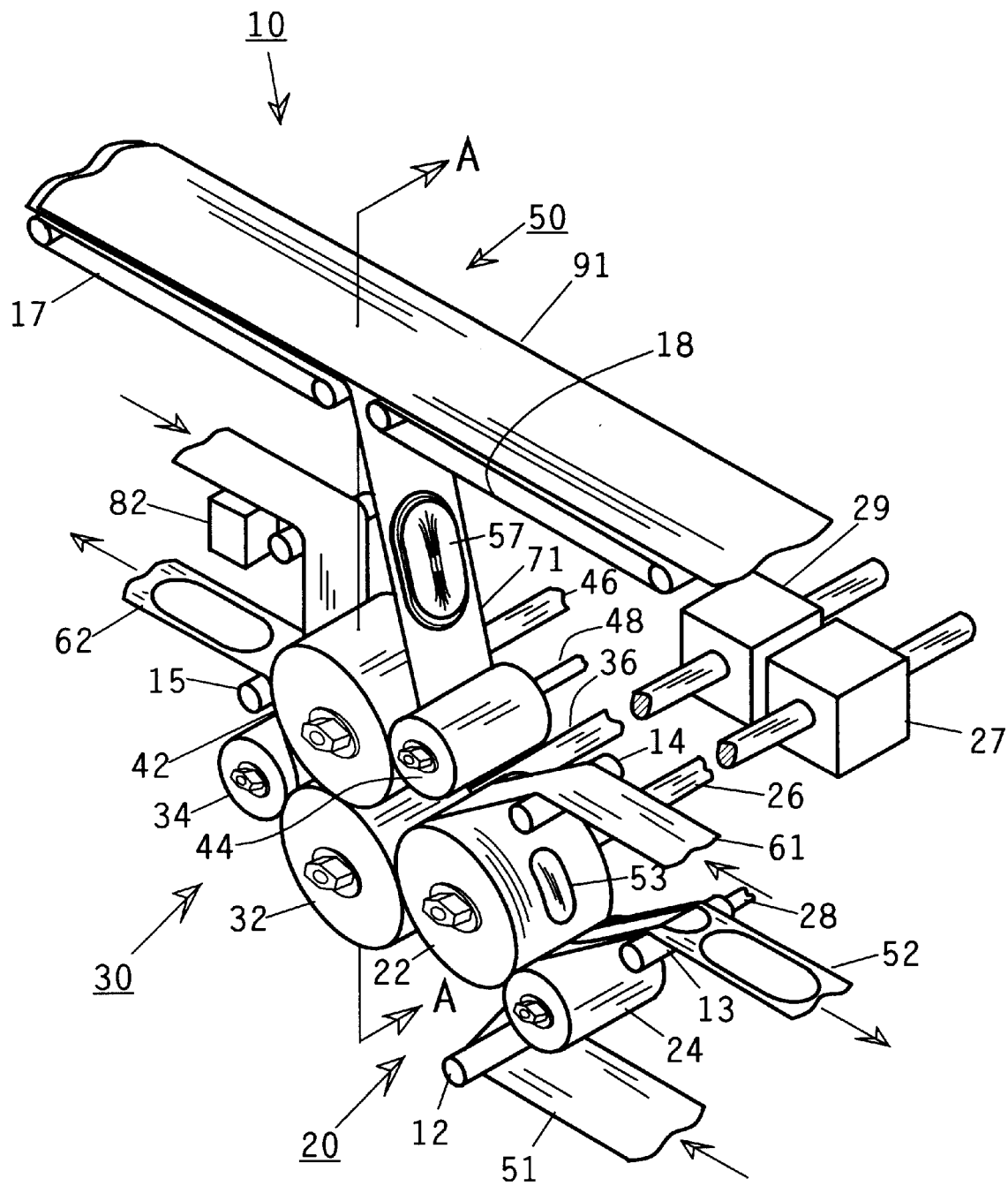
FIG. 1 shows, in a perspective view, a schematic representation of one embodiment of a machine of the present invention.

The invention is not limited in its application to the details or arrangement of the machine components or process steps set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals in the drawing figures are used to indicate like components.

DETAILED DESCRIPTION OF THE ILLUSTRATED EMBODIMENTS

One embodiment of a machine for carrying out the process of the present invention is represented in FIG. 1 which shows schematically a machine for depositing two components of differing lengths, cut from webs of material moving at different speeds, registered with respect to one another, and depositing them on a third web moving at a third velocity. Since the two components have different lengths, the webs from which each is cut and the apparatus for cutting each from its web and transferring the cut components to the next machine element, must move at different speeds. The machine of the invention provides for the mating and registration of the two components, as well as for the deposition of the mated components onto a third web which is moving at a speed different from that of either of the two webs from which the components were cut.

Figure 2:
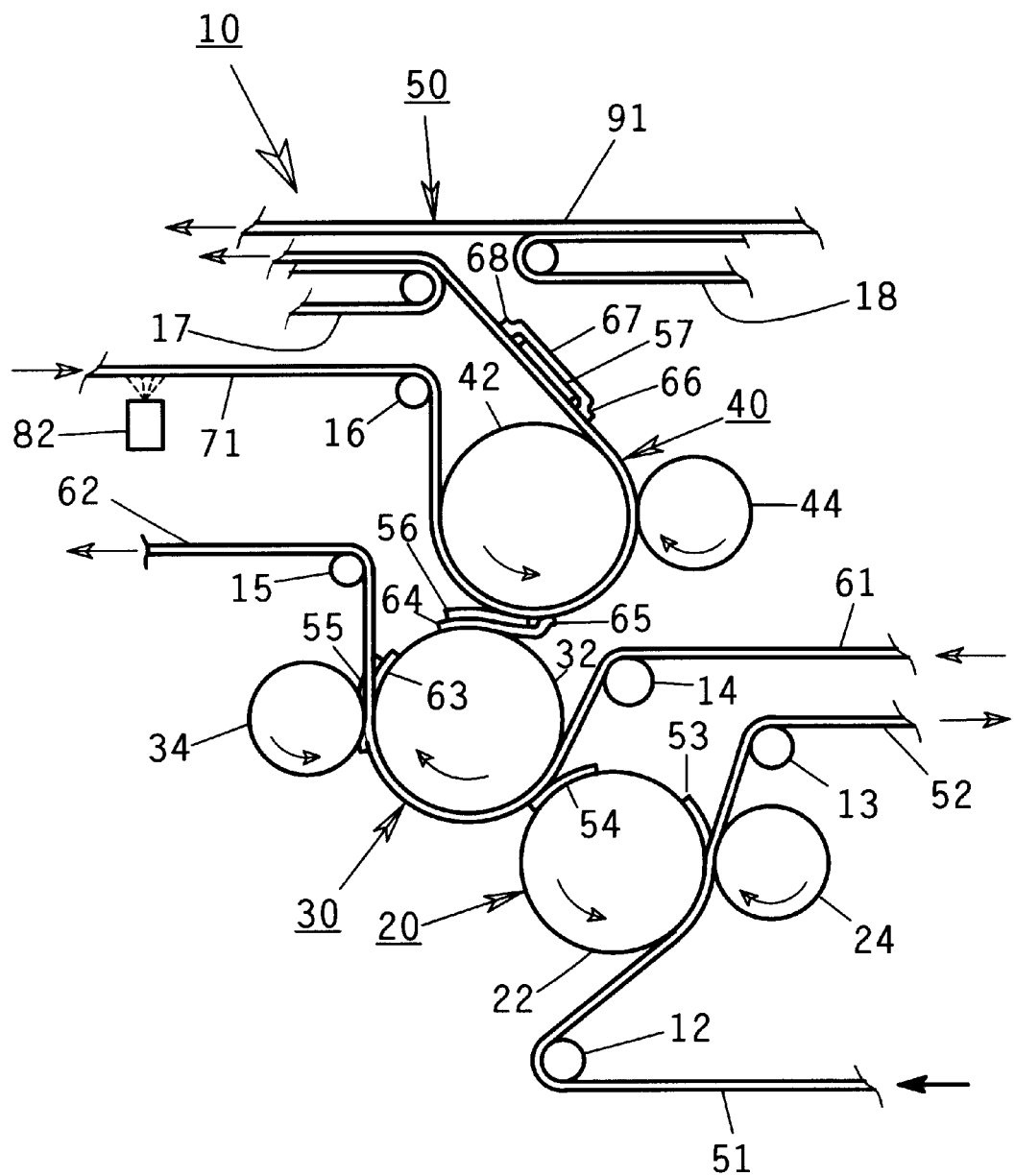
FIG. 2 shows the components and product webs moving through the machine of FIG. 1 in a side view taken along cut line A—A of FIG. 1.

Referring to FIGS. 1 and 2, the machine 10 comprises as its main components, a first component die cutting and transfer apparatus 20 comprising a combination die cut and transfer roller 22 and cooperating anvil roller 24. Combination die cut and transfer roller 22 is driven by shaft 26 attached to phase shift differential 27 which, in turn is attached to the machine line shaft. A second component die cutting and transfer apparatus 30, likewise comprises a combination die cut and transfer roller 32 and cooperating anvil roller 34. Combination die cut and transfer roller 32 is driven by shaft 36 attached to phase shift differential 29 which, in turn, is attached to the machine line shaft. An optional embossing apparatus 40 comprises embossing roller 42 and associated anvil roller 44, driven by the machine line shaft. A main product web transport apparatus 50 comprises conveyor belts 17 and 18, driven by the machine line shaft.

Embossing roller 42 and its associated embossing anvil roller 44 are driven at a constant speed equal to the machine line shaft speed and the speed of the product web 91, measured in terms of product per minute. First 22 and second 32 component die cut and transfer rollers and their respective cutter anvil rollers 24 and 34 are driven at constant speed in the manner detailed further below.

Referring to FIGS. 1 and 2, a web 51 of a first material is delivered under slight tension to roller 12. The material then passes between first component die cut and transfer roller 22 and die cut anvil roller 24 to cut the web 51 of first material into component pieces 53 having the desired shape and dimensions.

Figure 7:
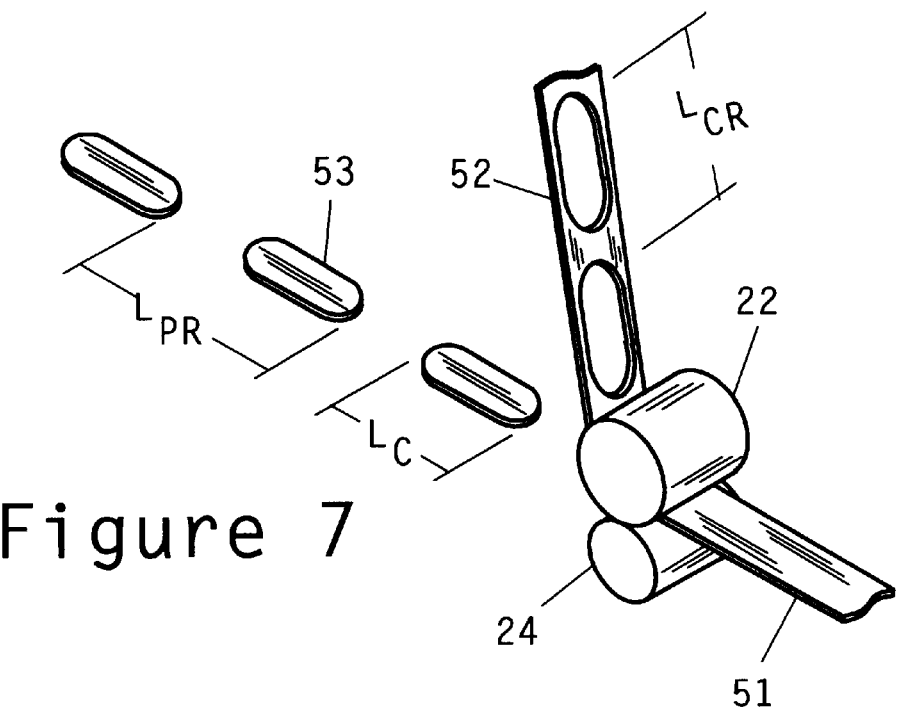
FIG. 7 shows a schematic representation of a die cut and anvil roller assembly for cutting a web of material by the "ladder cut" method.
Figure 8:
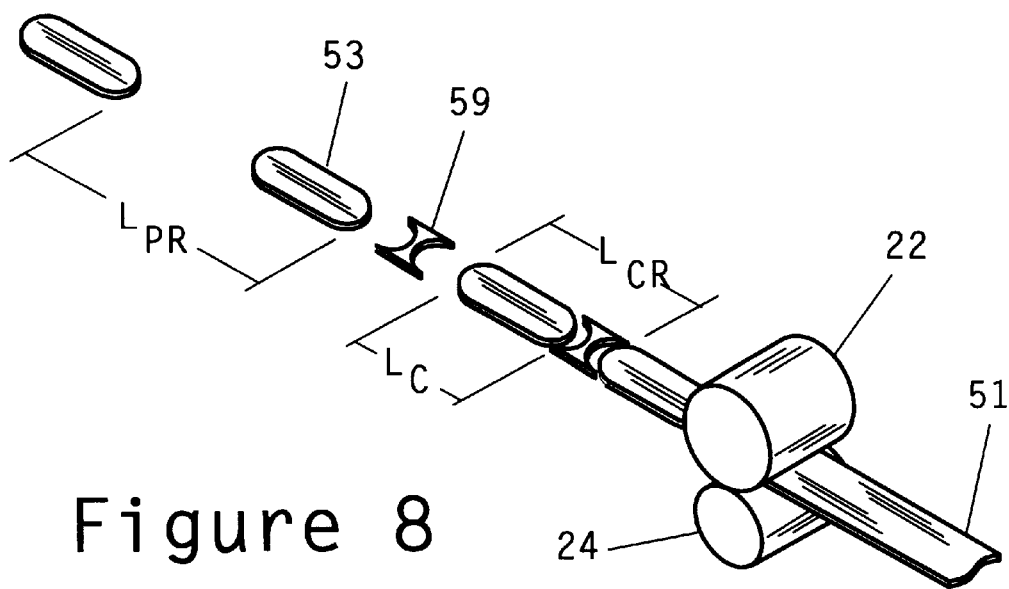
FIG. 8 shows a schematic representation of a die cut and anvil roller assembly for cutting a web of material by the "butterfly cut" method.

The "cookie cutter" blade on die cut and transfer roller 22 may be configured to cut component pieces by either a "ladder cut" method or a "butterfly cut" method as shown in FIGS. 7 and 8, respectively. The ladder cut method is depicted in a generalized manner in FIG. 7, where an advancing web 51 of material passes between die cut roller 22 and anvil roller 24. The scrap "ladder" 52 of cut web is shown moving up and away from the die cut and anvil rollers. A cut first component piece 53 is shown moving along the process stream away from the rollers. The lengths of the cut component pieces 53 are indicated in FIGS. 7 and 8 by the dimension $L_C$. The component repeat length, i.e. the distance between the leading edge of one cut component and the leading edge of the next following cut component, is indicated as $L_{CR}$ and the product repeat length, i.e. the distance between the leading edge of one completed product and the leading edge of the next following product in the process stream, is indicated at $L_{PR}$ which may or may not be the same as the component repeat lengths.

While shown in FIG. 7 as pieces having parallel sides and semi-circular ends, the component pieces 53, cut by the ladder cut method, may be of any desired shape. Since the web 51 of material in the ladder cut method is of a width greater than the width of the cut component pieces, there is a region of scrap in the ladder 52 along the sides of each component piece. Likewise, a scrap region of length $L_{CR}$–$L_C$ exists between successive component pieces. As a result, the component pieces 53 may be cut in any desired shape by the ladder cut method, as for example circular, elliptical, "dog-bone" shape, serrated, etc. While possessing the advantage of permitting the component pieces to be cut in any desired shape, the ladder cut method suffers, however, from the disadvantage of having more scrap than the butterfly cut method, which is depicted in FIG. 8.

In FIG. 8, an advancing web 51 of material is shown as passing between die cut roller 22 and anvil roller 24 to produce the component pieces 53 cut by the butterfly method. The scrap pieces 59 are smaller than those derived from the ladder cut method. The component length, component repeat length, and product repeat length, are indicated as $L_C$, $L_{CR}$, and $L_{PR}$, respectively, as in FIG. 7.

Since, in the butterfly cut method, the web of material 51 is the same width as the final cut component pieces 53, there is less scrap but the cut pieces are constrained to have the parallel sides of the web 51. However, in an alternative embodiment, the side edges of the advancing web of material to be cut by the butterfly method may be previously cut so that the sides of the web have a repeating pattern of any desired shape. It is a simple matter to match the cutting frequency in the die cut roller to the frequency of repetition of the side-cut pattern in the web to produce component pieces cut by the butterfly cut method, but having shaped side edges. This alternative adds, however, to the cost and complexity of the process and the option of cutting component pieces by the butterfly method from a web having parallel sides is preferred.

The butterfly cut method is also preferred in those instances where the web of material to be cut into component pieces is costly, and the amount of scrap generated by the cutting process is to be minimized.

Referring again to FIGS. 1 and 2, the figures show the first component web 51 being cut into component pieces by the ladder cut method, but as mentioned above, either the ladder cut or butterfly cut method may be used. During the step of cutting the first discrete components 53 from web 51, die cut and transfer roller 22 and its associated cutter anvil roller 24 move at the speed of advancing web 51. As the component is cut from the web, its leading edge is held to the surface of the die cut and transfer roller 22 by vacuum means internal to the roller 22, as well as by the natural tendency of the cut component to remain in the "cookie cutter" blade. This tendency of the cut component to remain in the cutter blade is used to advantage on both die cut transfer rollers as will be discussed below.

Once the component 53 is completely severed from the web 51, the component is transferred to web 61. A unique feature of the machine and process of the present invention is the transfer of the first cut component from a first die cut roller directly to a second die cut roller. By this means, the machine of the invention permits the cutting of components from the second web of material while the components already cut from the first web overly the second web of material. To assist in the transfer of the first cut component from the first die cut transfer roller, the vacuum internal to the first die cut roller is turned off and vacuum on the second die cut transfer roller is turned on. In addition, if needed or desired, the mechanism controlling internal air pressure in the first die cut transfer roller can be set at a pressure slightly above ambient to push the cut component out of the cookie cutter blade at the appropriate point in the rotation of the roller. This is done by appropriate placement of vacuum slugs in a side commutator vacuum system more fully described below.

A web of second material 61 passes over roller 14 and enters the slight gap between die cut and transfer roller 32 and anvil roller 34 and receives a previously-cut first component, shown as 54 in FIG. 2. Cut discrete first component 54, as it comes away from the first web 51 overlays, or lies on top of the web of second material 61. The terms "overlie," "overlay" or "lie on top of" with respect to the cut first components 54 mean the web of second material lies between the cut first component and the die cut and transfer roller 32.

Vacuum means, internal to die cut and transfer roller 32 holds both the web of second material and the cut first component 54 to roller 32 in the manner described below as roller 32 turns. As the second web of material 61 and the overlying first component 54 travel with die cut and transfer roller 32, they enter the gap between die cut roller 32 and anvil roller 34. A cut is made in the second web 61 of material as the overlying cut discrete first component, shown as 55 passes through the cutter gap between rollers 32 and 34.

The cut in the web of second material 61 may produce a cut second component piece which is of the same overall dimensions as the cut first components, or of different overall dimensions, either larger or smaller. The shape and dimensions of the cut second discrete component 63 will, of course be controlled only by the shape and dimensions of the die cut blade on the face of roller 32. Since the cut in the second web of material is made as both the second web 61 and the cut first component 55 pass between the die cut roller 61 and its associated anvil roller 34, a number of resulting cuts in the overlying first component may or may not be made, depending on the relative registration of the cut first component with the second component die cutter, and the shape and dimensions of the second die cut roller blade. In a preferred embodiment, the blade on the first die cut transfer roller 22 and that on second die cut transfer roller 32 are of similar shape. The term "similar shape" is used in the same sense as in referring to geometric shapes and is meant that the two cutter blades have the same contour whether of the same or different dimensions. For example, if one cutter blade is of a circular shape, the other is also, whether of the same or a different diameter; if one is of a "race track" shape, the other is also, whether of the same width and length dimensions or not; if one is of a "dog bone" shape, the other is also, whether larger or smaller than the other etc.

The various situations which can result are best seen by reference to Table 1 which presents a matrix of the possibilities. In Table 1, the term "longitudinal center" of the workpiece components means the point on a center line running through the workplace in the direction of the web or workpiece flow through the machine, mid-way between the leading and trailing edges of the workpiece. Similarly, the term "longitudinal center" of the cutter blade on the second cutter roller means a point on a center line running through the cutter blade in the direction of the web or workpiece flow through the machine, mid-way between the leading and trailing edges of the blade. The terms "leading edge" and "trailing edge," when referring to workpiece components or the second web cutter blade, mean, respectively, the up-stream and down-stream edges with regard to workpiece flow through the machine.

It is to be understood that the matrix of possibilities presented in Table 1 does not treat of the consequences to the relative widths and lateral placement of the two components with respect to one another. These are affected only by the predetermined parameters of 1) the widths of the first component and second component webs, 2) the width of the first and second component cutting blades on the respective cutting rollers, and 3) the lateral placement of the two webs with regard to the cutter rollers as the webs pass through the machine.

It is preferred that the cutter blades are centered longitudinally with respect to the first and second webs as they pass through the machine. It is particularly preferred that the first component cutter blade is narrower that the second so that the width of the cut first component is less than that of the second cut component. Likewise, it is preferred that the relative sizes of the first and second cut workpiece components and their relative registration is such that the leading edge of the second cut component leads that of the leading edge of the first cut component. In a particularly preferred embodiment, the first cut component is both narrower and shorter than the second cut component, and is centered with respect to the second component. In this way a peripheral band of the second cut component extends beyond the periphery of the first cut component around the entirety of both components. In another particularly preferred embodiment, the first and second component cutter blades are chosen to have sizes and shapes with respect to one another, and the registration of the first and second cut components such that the peripheral band of the second component extending beyond the periphery of the first cut component is uniform in width around the entirety of the two components.

TABLE 1

Effect on First Component by Die Cut Blade on the Face of Second Die Cut and Transfer Roller

| Placement and Length of First Component with Respect to Second Component | Length of first cut component is less than length of second cut component ($L_{C1} < L_{C2}$) | Length of first cut component is greater than length of second cut component ($L_{C1} > L_{C2}$) |
| --- | --- | --- |
| Longitudinal centers of first cut component and second component coincide when cut is made in second web | First component is longitudinally centered on second component; no cut is made in either end of first component | Leading and trailing edges of first component are cut again by second web cutter blade so that first component is the same length as the second component |
| Longitudinal centers of first cut component and second component do not coincide when cut is made in second web; leading edge of first component does not lead leading edge of die cut blade for second component | First component is longitudinally off-center on second component; no cut is made in either end of first component | Trailing edge of first component is trimmed so that first and second components are of equal length |
| Longitudinal centers of first cut component and second component do not coincide when cut is made in second web; leading edge of first component leads leading edge of die cut blade for second component | Leading edge of first component is trimmed to match the leading edge of the second component | a) If off-set in longitudinal centers of first component and die cut blade is less than to $L_{C1}-L_{C2}$, both the leading and trailing edges of first component are cut again by second web cutter blade so that first component is the same length as the second component; b) If off-set in longitudinal centers of first component and die cut blade is greater than to $L_{C1}-L_{C2}$, the leading edge of first component is cut again by second web cutter blade |
| Longitudinal centers of first cut component and second component do not coincide when cut is made in second web; trailing edge of first component trails trailing edge of die cut blade for second component | Trailing edge of first component is trimmed to match the trailing edge of the second component | a) If off-set in longitudinal centers of first component and die cut blade is less than to $L_{C1}-L_{C2}$, both the leading and trailing edges of first component are cut again by second web cutter blade so that first component is the same length as the second component; b) if off-set in longitudinal centers of first component and die cut blade is greater than to $L_{C1}-L_{C2}$, the trailing edge of first |

TABLE 1-continued

Effect on First Component by Die Cut Blade on the Face of Second Die Cut and Transfer Roller

| Placement and Length of First Component with Respect to Second Component | Length of first cut component is less than length of second cut component ($L_{C1} < L_{C2}$) | Length of first cut component is greater than length of second cut component ($L_{C1} > L_{C2}$) |
| --- | --- | --- |
| | | component is cut again by second web cutter blade |

By indexing the die cut rollers 22 and 32 with respect to one another, the first component piece can be controllably registered with respect to the second component piece so that the first piece is centered on the second, or, in such a manner that the leading end of the advancing first piece leads or trails the leading edge of the second piece by any desired amount. This indexing is achieved in a manner well understood in the mechanical arts by interposing between the machine line shaft and the shaft driving either or both die cut roller 22 or 32 a phase shift differential of the type manufactured by Fairchild Industrial Products Co., 1501 Fairchild Drive, Winston-Salem, N.C., USA under the trade name "Specon®." Phase shift differentials 27 and 29 are shown in FIG. 1 attached to shafts 26 ad 36 driving die cut and transfer rollers 22 and 32, respectively. This arrangement permits adjusting the phase angle between die cut rollers 22 and 32 to advance or delay the cutting of one of the components with respect to the other.

Returning to the description of the flow of the webs and workpiece components through the machine as depicted in FIGS. 1 and 2, once the second component is completely severed from the web of second material 61, the stacked first and second components are transferred to web 71.

The stacked first and second cut components, held to the surface of the die cut and transfer roller 32 by vacuum means internal to the roller, and by the natural tendency of the second cut component to remain within the "cookie cutter" blade, are moved into the gap between die cut and transfer roller 32 and an optional embossing roller 42. A web of third material 71, under slight tension, is shown in FIG. 2 entering the machine over roller 16 after having received an application of adhesive from adhesive applicator 82. The adhesive employed is chosen for its suitability to the materials making up the first, second and third webs of material after the manner well known in the diaper and feminine care article art.

The stacked cut first and second components are pressed to the web of third material 71 in the gap between roller 32 and roller 42. As shown in FIG. 2, stacked first component 56 and second component 64 are shown in the gap between the two rollers. The surface of first component 56 next adjacent the web of third material 71 is held to web 71 by the previously-applied adhesive, as is the edge of the larger second component 64 which protrudes around the first component 56. As indicated in FIG. 2, the leading edge 65 of second component 64 is shown adhered to the web 61 of third material as the stacked pair of components are shown leaving the gap between rollers 32 and 42.

The stacked cut first and second workpiece components next pass through the gap between optional embossing roller 42 and embossing roller anvil 44 to emboss a pattern, if desired, upon the two stacked components and the web of third material 71. An adhesive application is applied to the surface of web 71 by adhesive applicator 82. The stacked cut components are held to the surface of web 71 by the adhesive as the two component are transferred to web 71. As web 71 and the stacked cut components pass through the gap between embossing roller 42 and embossing roller anvil 44, the pressing action of the two rollers forms a complete seal between web of third material 71 and the edge of the cut second component which protrudes outwardly from the edge of the cut first component. This action forms a "sandwich" in which the smaller cut first component is sealed between the cut second component and the web of third material. The embossing in the sandwich of cut components is enabled by providing the working surface of the press roller with either a raised or depressed pattern which imparts to the sandwich the corresponding negative of the pattern disposed on the press roller working surface. The embossing step is optional and, if not desired, can be eliminated by simply making the face of roller 42 smooth rather than having an embossing pattern.

Third web 71, now bearing the first and second cut workpiece components (shown as element 57 in FIG. 2) bonded to the web surface, are next received on conveyor belt 17 where the third web and components are mated with a fourth web 91 bearing additional components of the product, assembled up-stream from the machine assembly shown in FIG. 1. As the third web 71 and fourth web 91, each bearing their respective components move downstream, additional operations, as needed or desired, are performed on both webs. These operations may include, for example, bonding the third and fourth webs to one another by conventional means known in the art, and adding addition product components to the upper surface of fourth web 91 such as the garment adhesive strip and adhesive peel strips, shown as elements 93 and 92, respectively, in FIGS. 10 and 11.

Figures 3, 4:
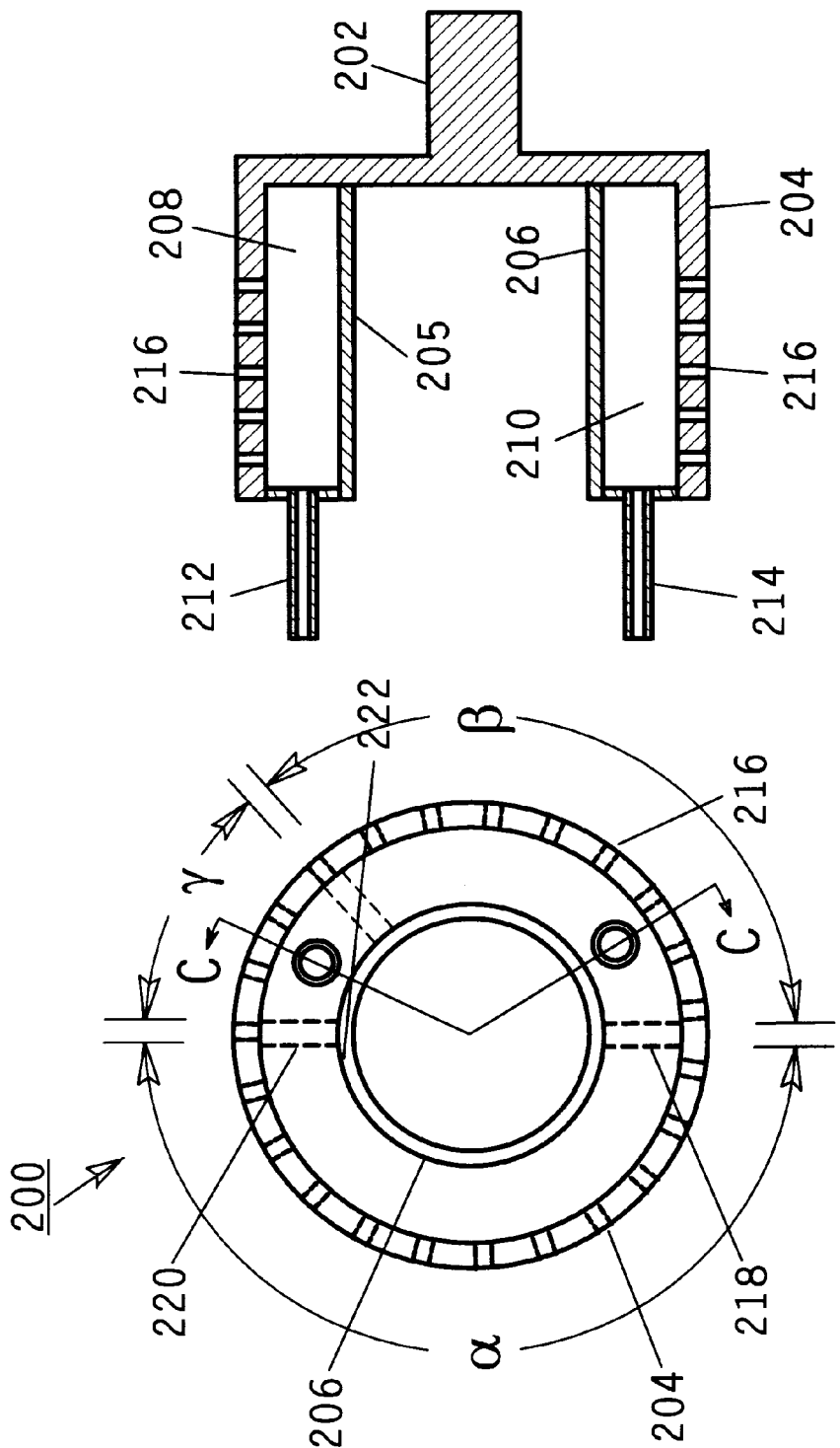
FIG. 3 is an end view of of a side commutator vacuum system employed in the illustrated embodiment of the machine of FIG. 1.
FIG. 4 shows a cross sectional view of the commutator of FIG. 3 taken along cut line C—C of FIG. 3.

The vacuum systems employed for holding cut workpiece components to the die cut and transfer rollers employ conventional vacuum systems well known in the art. These are illustrated generally in FIGS. 3–6. FIG. 3 shows an end-view of a so-called "side-commutator" vacuum system 200. FIG. 4 shows the vacuum system of FIG. 3 in a cross-section taken along cut line C—C.

Referring to FIG. 4, the system comprises a stationary commutator made up of two sections 205 and 206. The upper section in FIG. 4 comprises a chamber 208 and tube 212 through which high vacuum is introduced into chamber 208. The lower section 206 of the commutator in FIG. 4 comprises a chamber 210 into which low vacuum is introduced through tube 214.

Referring to FIG. 3, baffles 218, 220, and 222 are shown which divide the commutator into three chambers: a chamber into which no vacuum is introduced, a chamber of low vacuum, and a chamber of high vacuum. These chambers correspond to the arcs α, β, and γ, respectively. Unlike the side-commutator system described below, in the center commutator system, vacuum is maintained in the low and high vacuum chambers at all times, while the radial holes 216 in concentric rotor 204 move past each chamber. In this way, no vacuum, low vacuum, or high vacuum is introduced to the outer surface of the rotor 204 sequentially as the rotor 204 turns through each revolution on shaft 202.

The lengths of arcs α, β, and γ, are determined, and can be changed by, movement of the baffles 218, 220, and 222. The center-commutator system 200, with its capability of having zones of non vacuum, low vacuum, and high vacuum, is well adapted for rollers in the machine of the invention where it is necessary to turn on and turn off vacuum, and to have regions of high vacuum as, for example in the die cut and transfer roller 32 where both the first and second cut workpiece components need to be held to the surface of the roller.

Figures 5, 6:
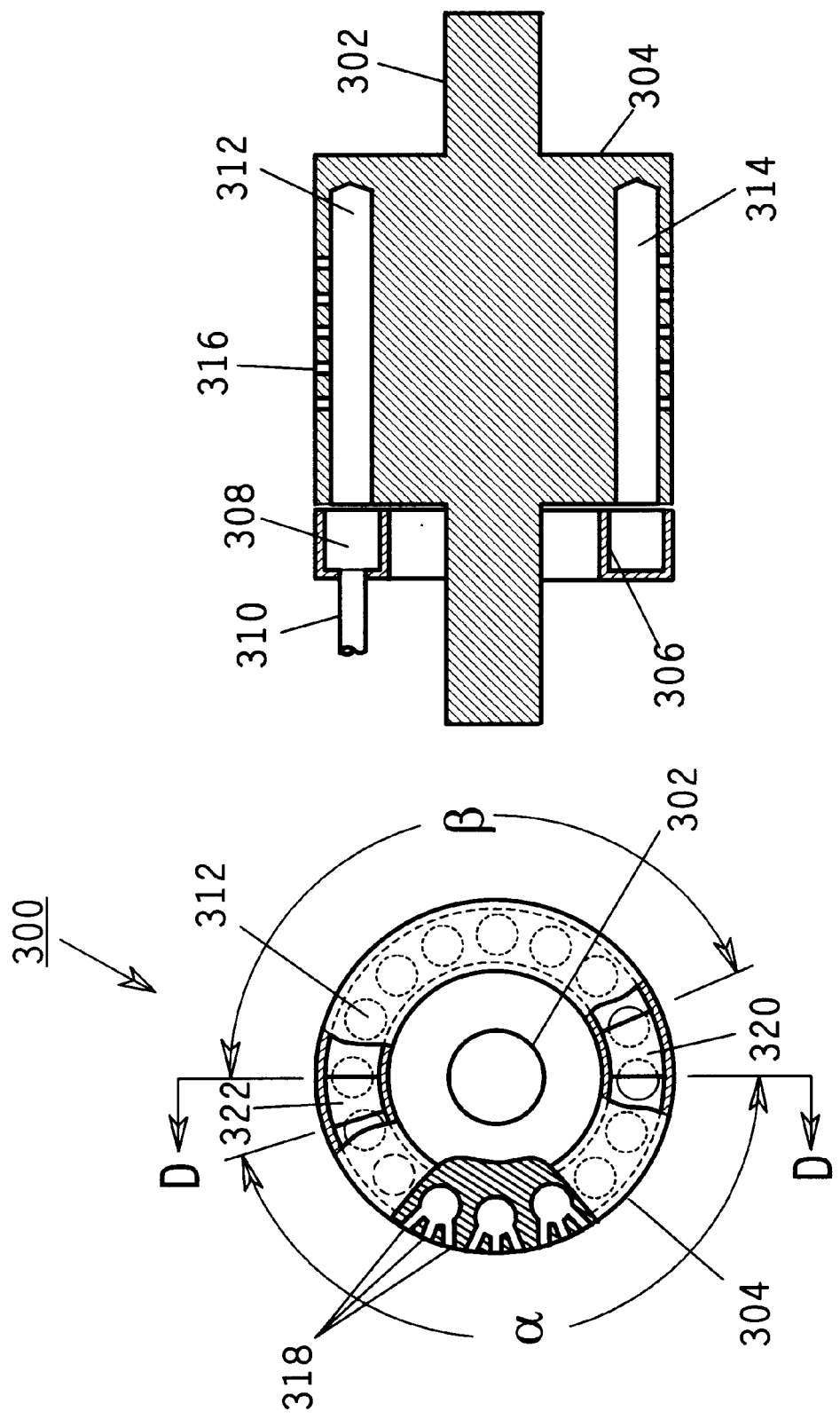
FIG. 5 shows an end-view of a center commutator vacuum system employed in the illustrated embodiment of the machine of FIG. 1.
FIG. 6 shows a cross sectional view of the commutator of FIG. 5 taken along cut line D—D of FIG. 5.

FIG. 5 shows an end-view of a so-called "center commutator" vacuum system 300. In the figure, the vacuum system comprises a stationary commutator 306 and rotor 304. The rotor 304 has a series of tubular holes 312 and 314 drilled into it, parallel to the axis of rotation of the rotor 304. Holes 316, and 318 drilled radially in the rotor 304 connect the axial tubes or holes 312 and 314 to the outer surface of the rotor. Vacuum is introduced into the commutator through entry tube 310 in the zone between the vacuum slugs 320 and 322.

Referring to FIG. 5, vacuum slugs 320 and 322 block the connection of the commutator 306 to the axial tubes 312 and 314 in the rotor 304 during a fraction of each rotation of the rotor. Thus, vacuum is introduced into tubes 312 and 314 of the rotor only during that portion of each rotation of the rotor designated by the arc β when no vacuum slug is interposed between the commutator 306 and the rotor 304. The moveable vacuum slugs 320 and 322 determine the ends of vacuum zone defined by the arc β. The lengths of the arcs α and β can be adjusted by appropriate placement of the vacuum slugs. The side-commutator system 300 is well adapted for rollers in the machine of the invention where it is necessary to provide firm support for the roller, for example in the die cut roller 22.

While there has been shown and illustrated one embodiment of the machine of the invention for depositing and registering two workpiece components of differing length on one another and subsequently onto a constantly moving web of material, it will be readily seen by one of ordinary skill in the mechanical arts that the machine can be modified to introduce and register third, fourth, fifth, etc. workpiece components by simply introducing additional components of type illustrated in FIG. 3 and described above into the machine either up-stream or down-stream in the process from the corresponding elements shown. In this manner, the machine of the present invention provides an efficient and cost-effective device for manufacturing multi-component articles of manufacture where there is a need to "stack" up and register workpiece components and subsequently deposit them with registration on a constantly moving web.

Having thus described the machine and process for cutting and stacking, with registration, two discrete workpiece components of different lengths and depositing them on a constantly moving web, the following example illustrates the use of the process and machine of the invention for the manufacture of a multi-layer feminine hygiene napkin.

EXAMPLE

Figure 9:
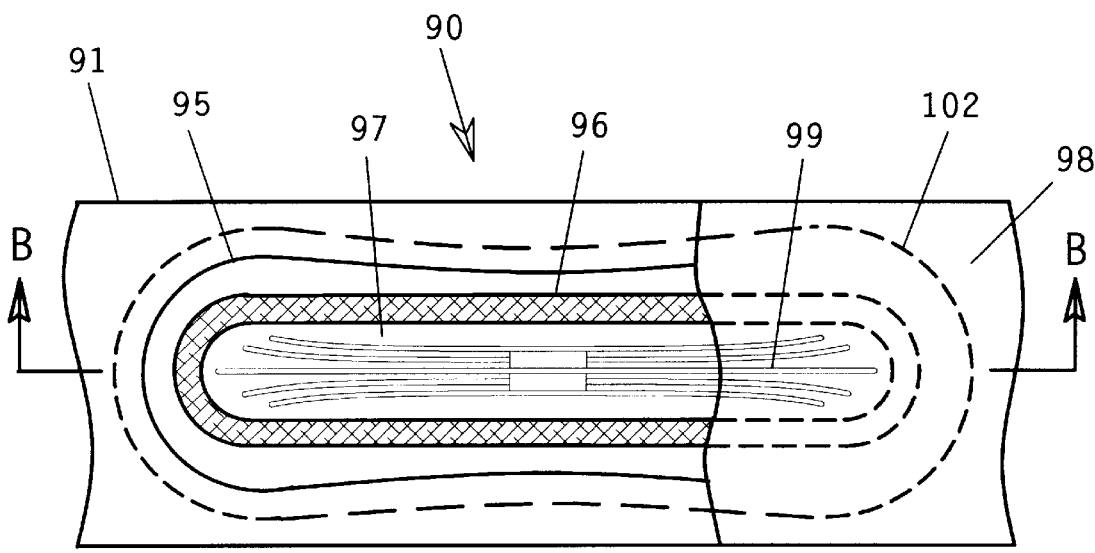
FIG. 9 shows a partially cut-away plan view of a so-called "mini" sanitary napkin produced by the machine and process of the present invention.
Figure 10:
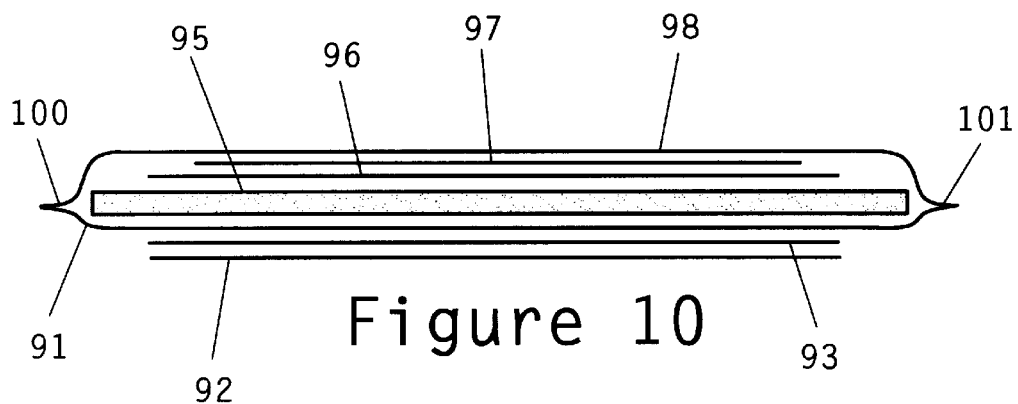
FIG. 10 shows a cut-away side view of the sanitary napkin of FIG. 9 taken along cut line B—B of FIG. 9.

A so-called ultra-thin or "mini" napkin, suitable for use by a woman during days of light menstrual flow, is depicted schematically in plan view in FIG. 9 and in schematic cross-sectional side-view in FIG. 10. The cross-sectional view in FIG. 10 is taken along cut line B—B of FIG. 9. A thicker or so-called "maxi" napkin, suitable for use by a woman during days of higher menstrual flow, is depicted in schematic cross-sectional side view in FIG. 11 where the napkin includes a super-absorbent pleget, 94 in addition to the same elements as the mini napkin of FIG. 10.

In FIG. 9, the elements of the napkin, shown in plan view, are built up from the lowest garment-side "barrier component" to the uppermost body-side "cover" component of the napkin. The cover component of the napkin, made of a material of a type well known in the art, is permeable to body fluids and is the component of the napkin worn closest to the user's body during use. The barrier component, also made of materials of a type well known in the art, is of an impermeable material and is worn furthest from the user's body, next to the undergarments.

Figure 11:
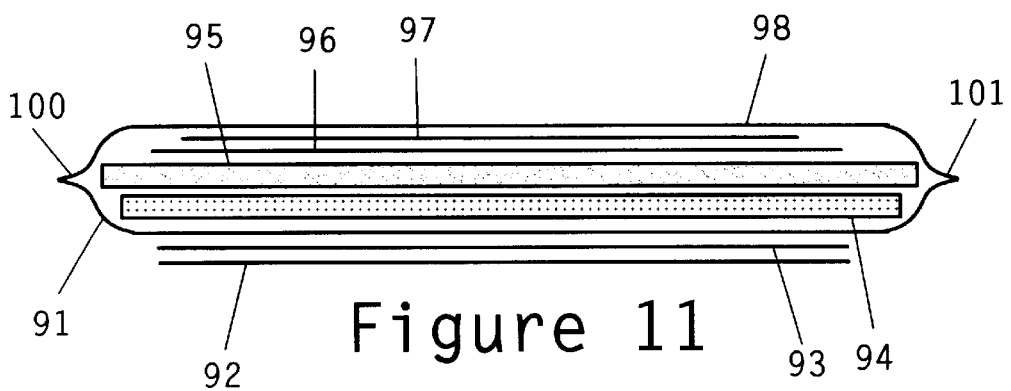
FIG. 11 is a cut-away side view of a so-called "maxi" sanitary napkin as in FIG. 9, showing the additional component of a super-absorbent pleget 94.
Figure 12:
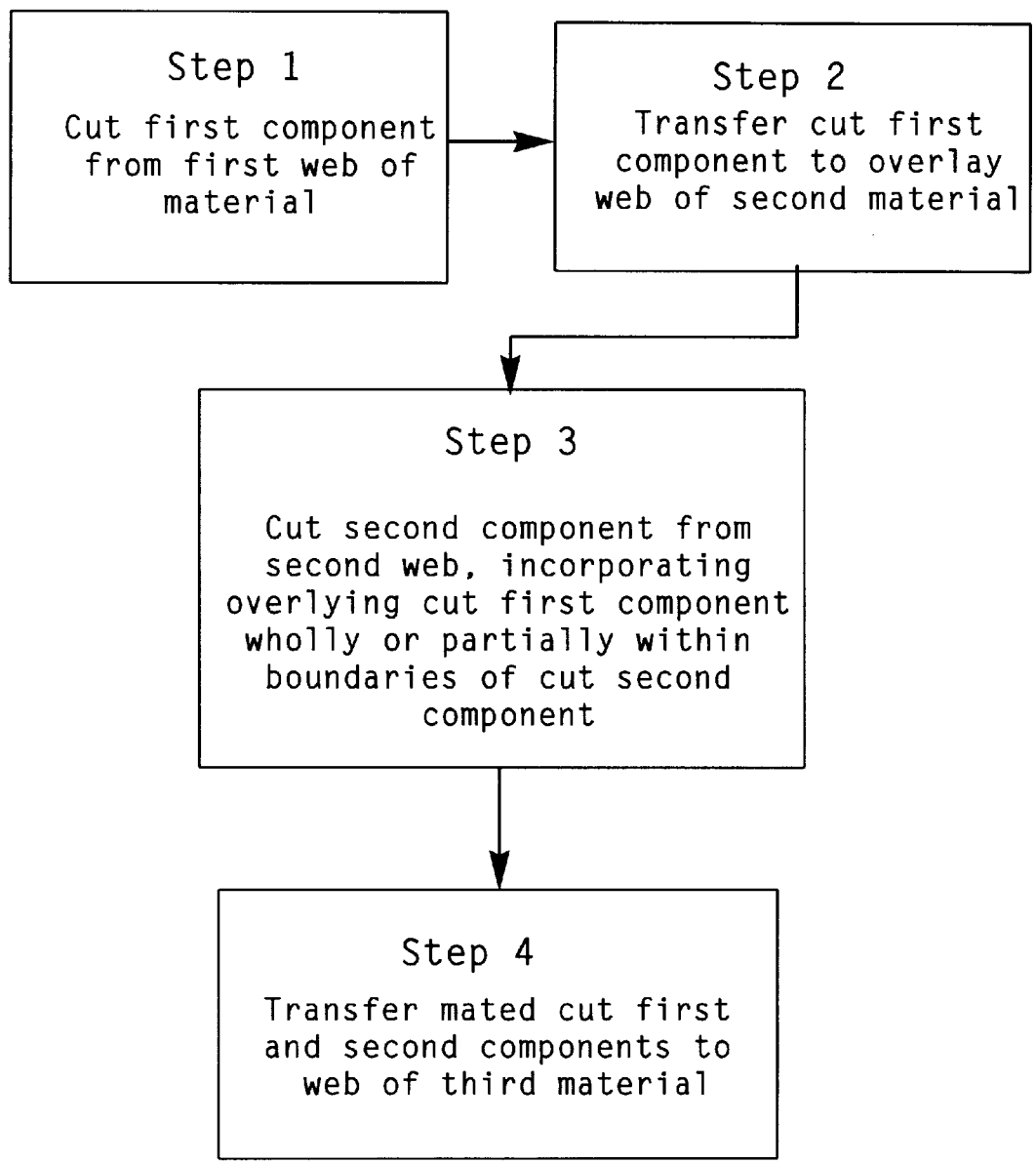
FIG. 12 is a representation of the general steps a process utilizing the machine of the present invention.
Figure 13:
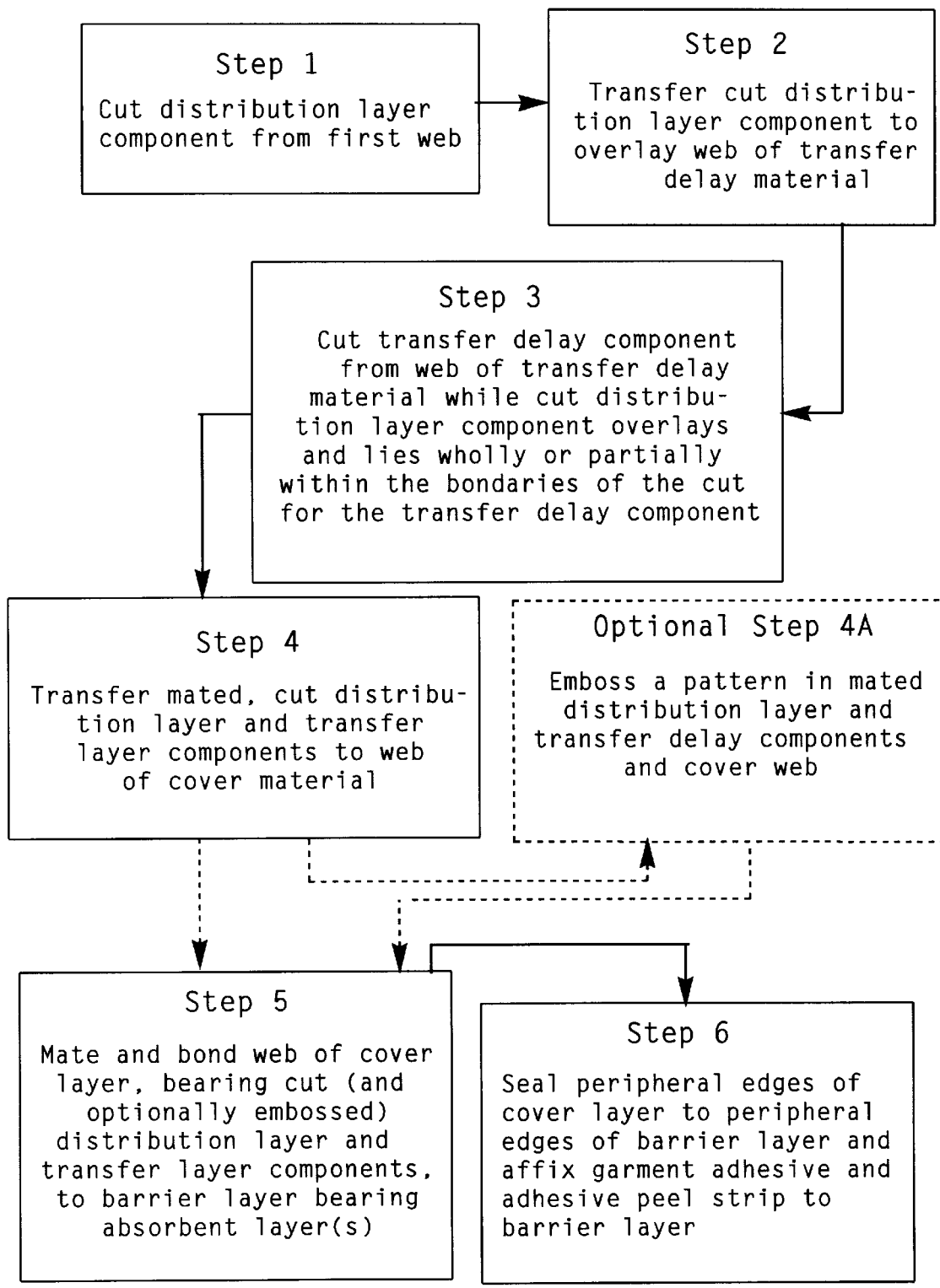
FIG. 13 is a representation of the steps of manufacturing a sanitary napkin utilizing the machine of the present invention.

The napkin 90 depicted in FIGS. 9, 10, or 11 and described in this Example comprises a unique distribution feature which serves to disseminate, or distribute, body fluids prior to their reaching the absorbent component of the napkin in order to provide a more efficient napkin having longer service life prior to the need for its replacement and resulting greater comfort to the user. The distribution feature includes distribution and delay components not found in prior art napkins. The specific materials used for the various components of the napkin are described in detail in co-pending application Ser. No. (Attorney's Docket No. 13303.10), the contents of which are incorporated herein by reference.

In the napkin shown in FIGS. 9–11, the cover layer 98 corresponds to the third web of material described in the general process detailed above. The distribution layer component 97 corresponds to the first cut component, and the transfer delay component 96 corresponds to the second cut workpiece component. The barrier layer 91 corresponds to the web of fourth material, and absorbent layers 95 and 94, adhesive strip 93 and adhesive peel strip 92 correspond to elements attached to the barrier layer 91 in process steps not part of this invention.

In this Example, specific lengths of the napkin and each component will be given to aid in understanding the invention. However, it is to be understood that the specific dimensions are cited merely for illustrative purposes and should not be read as limiting the scope of the invention as it is defined by the appended claims.

Referring to FIG. 9, the napkin 90 has, when finally cut along dashed cut line 102, a dog-bone shape and an overall length $L_P$ equal to about 300 mm. With, for example, an allowance for in-process strain of 2 percent and a scrap of 3 mm between successive finished napkins when they are cut along dashed line 102, the product repeat length $L_{PR}$ is 306 mm. The napkin 90 comprises an upper cover layer 98 which is permeable to body fluids. Cover 98 constitutes the moving web of material 71 mentioned in the general process discussion above.

Directly under the cover layer 98 there is a distribution component 97 of length, $L_{C2}$, about 254 mm and component repeat length, $L_{CR2}$, of about 260 mm fabricated of a material which serves as a wicking agent to aid in the more or less uniform distribution of body fluids to the absorbent component below.

Directly under the distribution component 97 there is a transfer delay component 96 of length, $L_{C1}$, about 268 mm and component repeat length, $L_{CR1}$, of about 275 mm which is somewhat less permeable to body fluids than the cover layer 98. Transfer delay component 96 acts to slightly retard the flow of body fluids to permit the distribution component 97 above to effectively carry out its wicking function prior to the passage of body fluids through to the absorbent component 95 below. Lying under the absorbent layer 95 in the mini napkin of FIGS. 9 and 10 is the fluid impermeable garment-side or barrier layer 91.

In the maxi napkin of FIG. 11 the same elements, bearing the same reference numerals, are also present, however, a super-absorbent pleget component 94 is shown interposed between the absorbent layer 95 and the barrier layer 91. Both the mini and maxi napkins of FIGS. 10 and 11 are shown with the upper cover layer 98 sealed to the lower barrier layer 91 by seals 100 and 101 in the conventional manner. Also conventional garment adhesive strip 93 and protective adhesive peel strip 92 are shown for both napkins.

Referring again to FIGS. 9, 10, and 11, under the transfer delay component 96 there is the absorbent component 95. The barrier component 91, laying under the absorbent component 95, is typically made of a polymeric material which is not permeable to body fluids and which serves to shield the user's undergarments from staining by body fluids.

In the napkin 90 depicted in FIG. 9, the cover component is generally translucent and is typically made of a white material. To provide the consumer with visual cues that the napkin being purchased has the distribution feature mentioned above, the absorbent layer 95, transfer delay component 96 and distribution component 97 are fabricated of materials of different colors. For example, the absorbent component 95 and distribution component 97 may be white, while the transfer delay component 96 may be light blue, pink, peach, or some other pleasing color. The various components, viewed through the preferably translucent cover component 98 thus form a pleasing pattern. The cross-hatched region of the transfer delay component 96 in FIG. 7 appears as a uniform band of color through the translucent upper cover component 98. To add to the visual cues, the finished napkin 90 may be further embossed with a visual cue pattern 99.

It is highly desirable that the distribution component 97 and the transfer delay component 96 be carefully registered with respect to one another, and with the optional embossed visual cue 99. If the distribution component 97 and transfer delay component 96 are mismatched, the colored band is seen as a non-uniform band and detracts from the overall aesthetic appearance of the finished product. Moreover, if the optional embossed visual cue pattern 99 is similarly mismatched with the band of color, the overall pleasing appearance of the product is diminished.

Referring to the specific components with exemplary dimensions given above, the details of the general process for making the feminine napkin of this invention become clear with reference to FIGS. 1 and 2. A web of cover material 71 for the napkin 90 is fed to the machine of the invention at a constant speed of $L_P$ per repeat or 306 mm/repeat. A web of first component material 51 from which the distribution layer components are cut is fed to the pair of die cut and anvil rollers 22 and 24 at a constant speed of $L_{CR1}$ per repeat, or 260 mm/repeat. A web 61 of second material is fed to anvil and die cut rollers 32 and 34 at a constant linear speed of $L_{CR2}$ per repeat, or 275 mm/repeat, to be cut into distribution components.

Once the distribution layer component 53 is cut free from web 51, and component 53 is fed onto the web 61 of transfer delay material, the web 61 is cut with the first component overlaying the second in the manner detailed above.

When the second component (63 in FIG. 2), and its overlying first component (55 in FIG. 2) are free of web 61, the stacked pair of components is transferred to web 71.

As shown in FIGS. 1 and 2, embossing and anvil rollers 42 and 44 apply an optional embossed visual cue pattern 99 to the partially finished napkin.

While there have been shown and exemplified preferred embodiments of the process and machine of the present invention, it will be clear to those skilled in the art that various departures may be made from the preferred embodiments of both the machine and process without departing from the scope of the invention as defined by the appended claims.

What is claimed is:

1. A machine for manufacturing a multi-component product comprising at least two components cut from moving webs of material, each of said components having a shape and associated dimensions including a length, a leading and a trailing edge, a longitudinal center line, and a longitudinal center defined by a point midway on said longitudinal center line between said leading and said trailing edge; registering the components with respect to one another; and depositing the registered components on a web of moving material, said machine comprising:

a) a first cutting and transfer apparatus for cutting first components from a first web of material moving at a first speed and transferring the first component to overly a second web of material moving at a second speed;

b) a second cutting and transfer apparatus for receiving the first components from said first apparatus on said second web of material and for cutting a second component from the second web while said first cut component overlies said second component, and for transferring the first and second cut components to a web of material moving at a third speed;

wherein said first cutting and transfer apparatus and said second cutting and transfer apparatus each comprise a combination die cut and transfer roller and an anvil roller, the combination die cut and transfer roller and anvil roller of each apparatus having cooperating working surfaces for cutting components from webs of material passing therebetween, the working surfaces of the combination die cut and transfer rollers of said first and second cutting and transfer apparatuses being in cooperative working relationship with one another to directly transfer a first component cut by said first cutting and transfer apparatus to overly said second web of material on said second die cut transfer roller prior to a component being cut from said second web by said second cutting and transfer apparatus.

2. The machine of claim 1 wherein said first and second apparatuses each comprise a first combination die cut transfer roller and an anvil roller, each roller having a working surface, said first and second die cut transfer roller working surfaces having respective first and second cutting blades disposed thereon having respective first and second shapes and first and second dimensions associated with said first and second shapes, which blades cooperate respectively with the working surfaces of said first and second anvil rollers to cut from respective first and second webs of material respective first and second components having respective first and second shapes.

3. The machine of claim 2 wherein said first and second cutting blades are of similar shapes.

4. The machine of claim 3 wherein the dimensions of said second cutting blade are larger than the dimensions of said first cutting blade.

5. The machine of claim 1 further comprising means for adjusting the longitudinal centers of said first and second components with respect to one another as said second component is cut from said second web of material.

6. The machine of claim 5 wherein said means for adjusting the longitudinal centers of said first and second components comprises phase shift differential apparatus driving one of said first and second apparatus.

7. The machine of claim 2 further comprising a third apparatus for receiving the cut first and second cut components on a third web of material.

8. The machine of claim 7 wherein said third apparatus comprises a press roller and an anvil roller, each having a working surface, said working surfaces cooperating to press the cut first and second components to said third web of material as said first and second cut components and third web pass therebetween.

9. The machine of claim 8 wherein said working surface of said press roller has a pattern for embossing a pattern into said first and second components.

10. The machine of claim 8 wherein the working surface of said press roller is in working relationship with the working surface of said second die cut transfer roller to transfer the first cut component overlying the cut second component directly to the web of third material.

11. A machine for manufacturing a multi-component product comprising at least two components cut from moving webs of material, each of said components having a shape and associated dimensions including a length, a leading and a trailing edge, a longitudinal center line, and a longitudinal center defined by a point midway on said longitudinal center line between said leading and said trailing edge; registering the components with respect to one another; and depositing the registered components on a web of moving material, said machine comprising:

a) a first apparatus comprising a first die cut transfer roller having a first cutter blade, and a first anvil roller, each of said rollers having a working surface, the first cutter blade of said first die cut transfer roller cooperating with the working surface of said first anvil roller to cut components from a first web of material passing therebetween and to transfer said cut components to overly a second web of material;

b) a second apparatus for receiving said first cut components on a second web of material, comprising a second die cut transfer roller having a second cutter blade, and second anvil roller, each of said rollers having a working surface, the second cutter blade of said second die cut transfer roller cooperating with the working surface of said second anvil roller to cut second components from said second web of material passing therebetween while said first cut components overly the second components;

the working surfaces of said first and second die cut transfer rollers being in cooperative working relationship with one another to directly transfer the components cut by said first die cut transfer roller to overly said second web of material on said second die cut transfer roller prior to a component being cut from said second web by said second die cut transfer roller.

12. The machine of claim 11 further comprising phase shift differential means for adjusting a rotational phase angle of said first apparatus with respect to said second apparatus to adjust the center point of said first component with respect to said second component as said second component is cut from said second web of material.

13. The machine of claim 12 wherein the working surfaces of each of said first and second combination die cut transfer rollers have respective first and second cutter blades having respective first and second shapes and respective first and second associated dimensions, said first and second cutter blades cooperating respectively with the working surfaces of said first and second anvil rollers to cut respective first and second components from respective first and second webs having corresponding first and second shapes and first and second corresponding associated dimensions.

14. The machine of claim 13 wherein said first and second cutter blade are of similar shapes.

15. The machine of claim 14 wherein the dimensions of said second cutter blade are larger than those of said first cutter blade.

16. The machine of claim 11 further comprising a third apparatus for receiving the cut first and second cut components on a third web of material, said third apparatus comprising a press roller and an anvil roller, each having a working surface, said working surfaces cooperating to press the cut first and second components to said third web of material as said first and second cut components and third web pass therebetween.

17. The machine of claim 16 wherein the working surface of said press roller is in cooperative working relationship with the working surface of said second die cut transfer roller to directly transfer the first and second cut components to a third web of material so that the first component lies between the cut second component and said third web of material.

18. The machine of claim 17 wherein said working surface of said press roller comprises a pattern for embossing said pattern in said first and second cut components as they pass between said press roller and the third apparatus anvil roller.

19. The apparatus of claim 16 wherein said third apparatus further comprises apparatus for depositing adhesive of said third web of material prior to said cut first and second being received on said third web.

20. A machine for manufacturing a multi-component product comprising at least two components cut from moving webs of material, each of said components having a shape and associated dimensions including a length, a leading and a trailing edge, a longitudinal center line, and a longitudinal center defined by a point midway on said longitudinal center line between said leading and said trailing edge; registering the components with respect to one another; and depositing the registered components on a web of moving material, said machine comprising:

a) first and second cutting apparatuses each comprising a combination die cut transfer roller and an anvil roller, the combination die cut transfer roller and anvil rollers of each apparatus having cooperating working surfaces for cutting components from webs of material passing therebetween, the working surface of the combination die cut transfer rollers being in cooperative working relationship with one another to directly transfer a component cut by said first cutting apparatus from a first web of material to overly a web of second material on said second die cut transfer roller prior to a component being cut from said second web by said second apparatus;

b) a third apparatus down-stream from said second apparatus comprising a press roller and an anvil roller, having cooperative working surfaces for receiving the first and second cut components on a third web of material and for embossing a pattern on said first and second components.

21. The machine of claim 20 further comprising means for adjusting the center points of said first cut component as it overlies said second component as said second component is cut from said second web of material.

22. The machine of claim 21 wherein said means for adjusting the center points of the first and second components comprises phase shift differential apparatus driving at least one of said first and said second die cut transfer rollers.

* * * * *